US010524914B2

(12) United States Patent
Pastorino et al.

(10) Patent No.: US 10,524,914 B2
(45) Date of Patent: Jan. 7, 2020

(54) THORACIC PROSTHESIS AND ITS METHOD OF PREPARATION

(71) Applicant: G21 S.R.L., San Possidonio (Modena) (IT)

(72) Inventors: Ugo Pastorino, Milan (IT); Filippo Foroni, Mirandola (IT); Michele Ferrotto, Pinerolo (IT)

(73) Assignee: G21 S.R.L., San Possidonio (IT)

( * ) Notice: Subject to any disclaimer, the term of this patent is extended or adjusted under 35 U.S.C. 154(b) by 516 days.

(21) Appl. No.: 15/070,527

(22) Filed: Mar. 15, 2016

(65) Prior Publication Data
US 2016/0270919 A1 Sep. 22, 2016

(30) Foreign Application Priority Data

Mar. 16, 2015 (IT) ................................ M2015A0397

(51) Int. Cl.
*A61F 2/28* (2006.01)
*A61F 2/30* (2006.01)
*A61B 17/80* (2006.01)
*A61B 17/82* (2006.01)

(52) U.S. Cl.
CPC ............ *A61F 2/28* (2013.01); *A61F 2/30965* (2013.01); *A61B 17/8076* (2013.01); *A61B 17/823* (2013.01); *A61F 2/3094* (2013.01); *A61F 2002/30957* (2013.01); *A61F 2240/005* (2013.01); *A61F 2250/0023* (2013.01)

(58) Field of Classification Search
CPC .......................... A61B 17/8076; A61B 17/823
See application file for complete search history.

(56) References Cited

U.S. PATENT DOCUMENTS

| 5,769,637 A | * | 6/1998 | Morgan | A61B 17/8071 433/176 |
| 2005/0288691 A1 | * | 12/2005 | Leiboff | A61F 2/0063 606/151 |
| 2011/0081397 A1 | * | 4/2011 | Skalla | A61F 2/0063 424/423 |
| 2011/0236459 A1 | * | 9/2011 | Stopek | A61F 2/0063 424/426 |

FOREIGN PATENT DOCUMENTS

| CN | 101601613 B | 4/2011 |
| CN | 102240233 A | 11/2011 |
| CN | 203379225 U | 1/2014 |
| JP | H04156840 A | 5/1992 |

OTHER PUBLICATIONS

Girotti P, Leo F, Bravi F, Tavecchio L, Spano A, Cortinovis U, Nava M, Pastorino U, The "Rib-Like" Technique for Surgical Treatment of Sternal Tumors: Lessons Learned From 101 Consecutive Cases, Ann Thorac Surg 2011; 92: 1208-16.*

* cited by examiner

*Primary Examiner* — Megan Y Wolf
(74) *Attorney, Agent, or Firm* — Pearne & Gordon LLP

(57) ABSTRACT

The present invention refers to a thoracic prosthesis constituted by a right hemisphere ED and a left hemisphere ES joined together, or to only one of the two hemispheres, or to only one portion of the latter. The present invention further relates to a method for the preparation of a synthetic thoracic prosthesis PT constituted by a right hemisphere ED and a left hemisphere ES joined together by only one of the two hemispheres or by a single portion of the latter; all of the above being prepared without any direct interaction with human body and prior to implantation therein.

8 Claims, 11 Drawing Sheets

THORACIC PROSTHESIS AND ITS METHOD OF PREPARATION

The invention refers to a thoracic prosthesis constituted by a right hemisphere ED and a left hemisphere ES joined together, or to only one of the two hemispheres, or only to a portion thereof. The present invention further relates to a method for the preparation of a synthetic thoracic prosthesis PT constituted by a right hemisphere ED and a left hemisphere ES joined together by only one of the two hemispheres or by a single portion thereof; all of the above being prepared without any direct interaction with human body and prior to being implanted therein.

Large intrathoracic tumors may occur with massive infiltration of the lung and chest wall to such an extent as to require pneumonectomy and partial or complete removal of the chest via a radical removal surgery. In the absence of an adequate reconstruction of the chest wall, this type of surgery may result in a serious risk of death to the patient due to a cardiopulmonary block.

STATE OF THE ART

A technique is known which is called "Rib-like technique" based on which an aluminum mould is used for the realization of thoracic cavity portions, e.g. some ribs and the sternum. The mould is a shaped support reproducing the ribcage in negative from the inside. In a first step, the inner mould is covered with a mesh, after which on this mesh an acrylic material is moulded at hand, which forms the chest portions to be recreated. The acrylic material is made to lie externally on the mesh without the latter being embedded internally thereof. One of the drawbacks of this technique is that it can only be used for small chest replacement portions, for example, the sternum and the anterior part of the ribs. On the other hand, it often happens that a large part of the chest, such as an entire hemisphere, is affected by the tumor and need to be replaced. Furthermore work by hand does not ensure accurate reproducibility and reliability that are instead required in many cases. Finally, the time requested for realizing the prosthesis is very variable and depends on the skill of the operator. Not least, the realization of the prosthesis is made in the operating room with the patient under general anesthesia.

Furthermore, notwithstanding the fact that said surface is covered with a mesh, it was found the problem of a difficult detachment of the acrylic material once the latter became solidified on the outer surface of the aluminum mould. For this reason solutions have been proposed which provide use of substances or materials promoting the detachment (release agents).

However, these substances are partly absorbed by the prosthesis and represent a source of toxicity for the patient. To overcome the drawback due to this toxicity, use of a Teflon coating was proposed that however causes a drift of the acrylic material during preparation of the prosthesis, due to which drift, the mesh becomes covered and impregnated, thereby coming to be occluded also in the intercostal space; this undesired phenomenon is absolutely to be avoided in that it reduces permeability of the intercostal space. The occlusion of the mesh within the intercostal space after the prosthesis has been implanted, causes stagnation of body fluids which were formed following transplantation, thus resulting in formation of infection and inflammation.

It is therefore deeply felt the need on the part of the operators of the sector, to have available a thoracic prosthesis as well as a cost-effective and simple method thereof, providing use of a material biocompatible with bodily fluids, tissues and organs; said prosthesis having adequate mechanical strength for ensuring total protection against impacts as well as a dynamic flexibility enabling correct functionality of the organs contained in said thoracic prosthesis once the same was implanted. Furthermore great emphasis is placed on the need to allow the fluids to flow within the intercostal space and the tissues to regrowth therein, which intercostal space must not be obstructed, in order that formation of fluid bags and stagnation of non-absorbed fluids is prevented which would cause formation of inflammation and infection.

SUMMARY OF THE INVENTION

The Applicant, after intensive and extensive research and development activity was able to select specific polymeric materials and to develop an innovative method of preparation, which provides use of a specific mould, owing to which it was possible to overcome the drawbacks and limitations affecting existing thoracic prosthesis and at the same time to adequately meet the needs referred to above.

The object of the present invention is a synthetic thoracic prosthesis PT having the characteristics according to the appended claim 1 and preferably constituted by a right hemisphere ED and a left hemisphere ES joined together only in the front part thereof by a connection sternal region RS, or only to one of the two hemispheres, or only to a portion of these hemispheres. The thoracic prosthesis PT of the invention is not limited to specific dimensions and can be either a prosthesis of the entire chest or a part thereof.

The presence of the reinforcement mesh-like structure RMS in the intercostal space SI, with the meshes being free, i.e. not occluded/clogged, advantageously allows an exchange of fluids, e.g. drainage fluids, from inside the thoracic prosthesis to the outside, as well as an improved integration of tissues, both of which aspects being postoperative conditions necessary for the purpose of a good healing. Owing to the presence of the perimetral frame T (SG1, SG2, SG3, SG4 and SG5) and the reinforcement mesh-like structure RMS which extends inside the rib-like elements Cn and the frame T, the prosthesis is reinforced, a reinforcement which is effective in both the extension direction of the rib-like elements Cn, and in the direction substantially perpendicular to this extension, i.e. in the direction in which the ribs-like elements are spaced apart from one another. Such reinforcement is further increased in the preferred embodiment of the prosthesis, wherein the reinforcement mesh-like structure is tensioned in the plane of its extension.

A further object of the present invention is a mould device 1 for the preparation of a synthetic PT thoracic prosthesis having the characteristics disclosed in claim 7. By providing grooves En and relief elements Rn as well as a perimetric groove Pn, all perfectly in register on both male and female portions of the mould, synthetic thoracic prosthesis PT may be obtained, which are free of any imperfections, such as burrs, within the intercostal spaces, which burrs would otherwise clog the reinforcement mesh-like structure, thus hindering passage of fluids (drainage fluids) and tissue integration.

Since, in a preferred embodiment, the mould device 1 exhibits a base 2 for housing the female portion 3 and/or a base 4 for housing the male portion 5, use can be made of only one device with moulds of various sizes. Additionally, because the material to be used for the base can be selected according to structural rigidity requirements and uniform application of the moulding pressure, whilst the material to be used for the mould can be selected based on criteria of alignment, tightness and easiness to detachment of the prosthesis from the inner surfaces of the mould, different materials for the base and the mould may be used.

Finally, in the preferred embodiment providing coupling means, the advantage is obtained of ensuring that the reinforcement mesh-like structure is always located at the center of the rib-like elements and the frame.

A further object of the present invention is a method for the preparation of a thoracic prosthesis having the characteristics according to claim 13, the prosthesis being prepared without any direct interaction with human body and prior to implantation therein.

By preparing the reinforcement mesh-like structure and making it to lie onto the surface of the male portion without any folds being formed, and by fastening said structure to the coupling means provided on the female portion of the mould, a perfect matching and superposition (adjustement) between the male and female portions can be obtained, owing to which thoracic prosthesis with almost perfect size and finish may be realized, which exhibit reproducible properties and are cost-effective. Further preferred embodiments of the present invention are disclosed in respective dependent claims and hereinafter described in detail without having to be construed as limiting the scope of the invention in any way whatsoever.

BRIEF DESCRIPTION OF DRAWINGS

FIG. 3B shows the ribs C1, C2, C3, C4, C5, C6, C7 and C8 (rib-like elements Cn), a meshwork (continuous element) of a synthetic material RMS and an outer closed frame T formed by five segments SG1, SG2, SG3, SG4 and SG5.

Each rib C1-C8 has a larger dimension and a minor dimension. The larger size runs along the minor axis, while the minor dimension runs along the major axis. The perpendicular section, compared to the larger size of each rib C1-C8, has an irregular elliptical shape which is more or less flattened along the minor dimension.

The ribs C1-C8 preferably have curved shapes, which generally differ from one another and further exhibit different extensions along the largest dimension thereof.

The ribs C1-C8 are spaced apart from one another in a substantially uniform manner along the larger dimension thereof and interspersed by a intercostal space SI. Synthetic material meshwork RMS portions (reinforcement mesh-like structure RMS) extend within the intercostal spaces SI, see FIG. 3B.

Figure 3A:
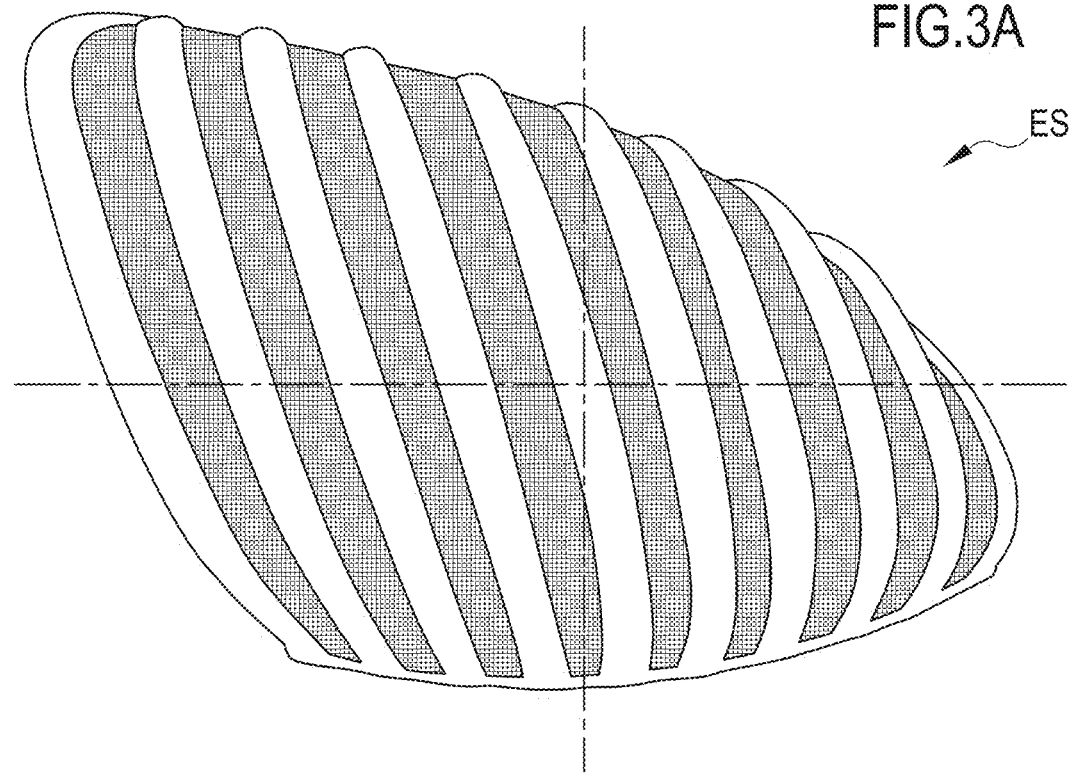
FIG. 3A shows an external view of a left hemisphere ES having a major axis which extends along the largest dimension from left to right, and a minor axis which extends along the minor dimension from the top downwards.
Figure 3B:
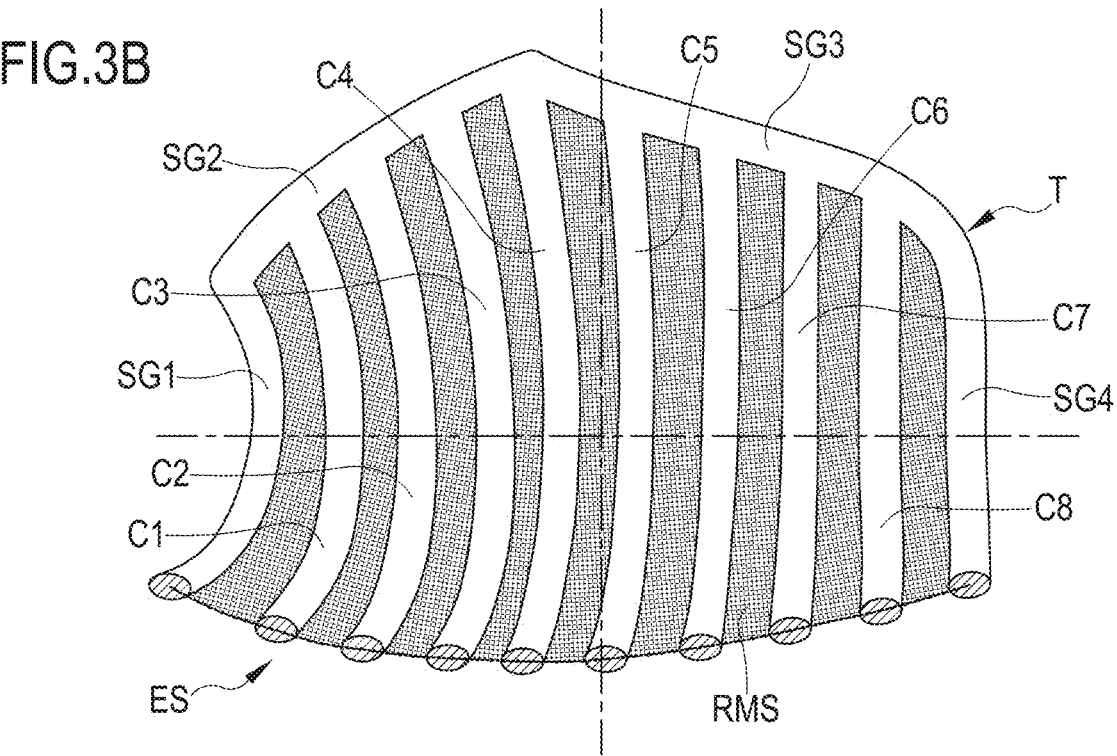
FIG. 3B shows an internal view of the same left hemisphere ES (FIG. 3A) which is obtained by a 180° rotation about the minor axis.

The synthetic material meshwork RMS is a continuous element passing through the ribs C1-C8 and intersecting the latter internally thereof, and fixed inside the SG1-SG5 segments forming a continuous closed frame T, see FIG. 3B.

The ribs C1-C8 are connected one to another along their major dimension via portions of said synthetic material meshwork RMS and along their lower dimension by the segments SG2, SG3 and SG5 which form part of the external closed frame T, see FIG. 3B.

The frame T is formed by five segments SG1, SG2, SG3, SG4 and SG5. The segment SG1 and SG4 are spaced apart from one another by the ribs C1-C8 and the intercostal spaces SI. Although part of the frame, said two segments SG1 and SG4 perform the functions of the first (upper) rib and last (lower) rib within the thoracic prosthesis PT, see FIG. 3B.

Figure 4:
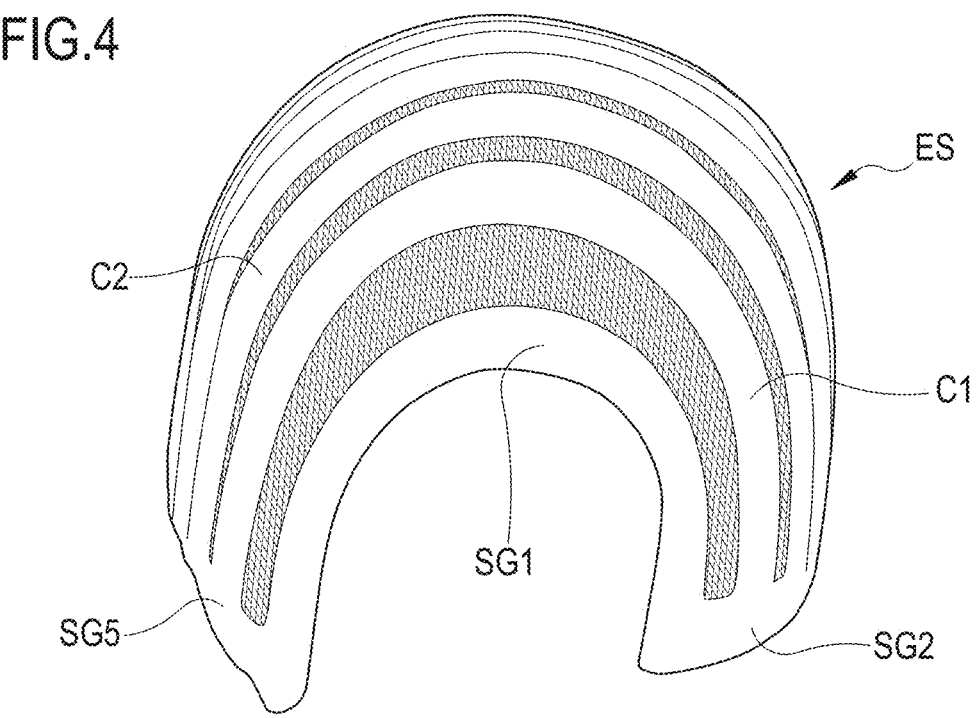

FIG. 4 shows a top view of the left hemisphere ES, in particular the segment SG1.

Figure 5:
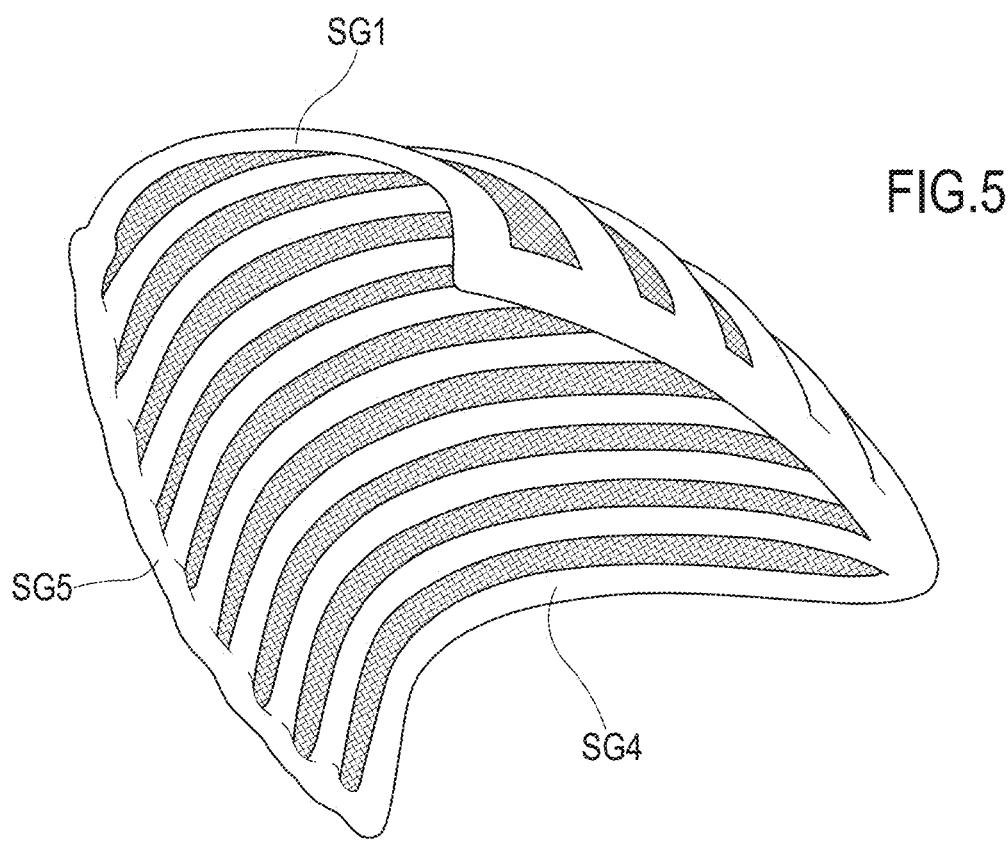

FIG. 5 shows an internal view of the left hemisphere ES, in particular the segment SG4 opposite to the segment SG1, and of the segment SG5.

Figure 6:
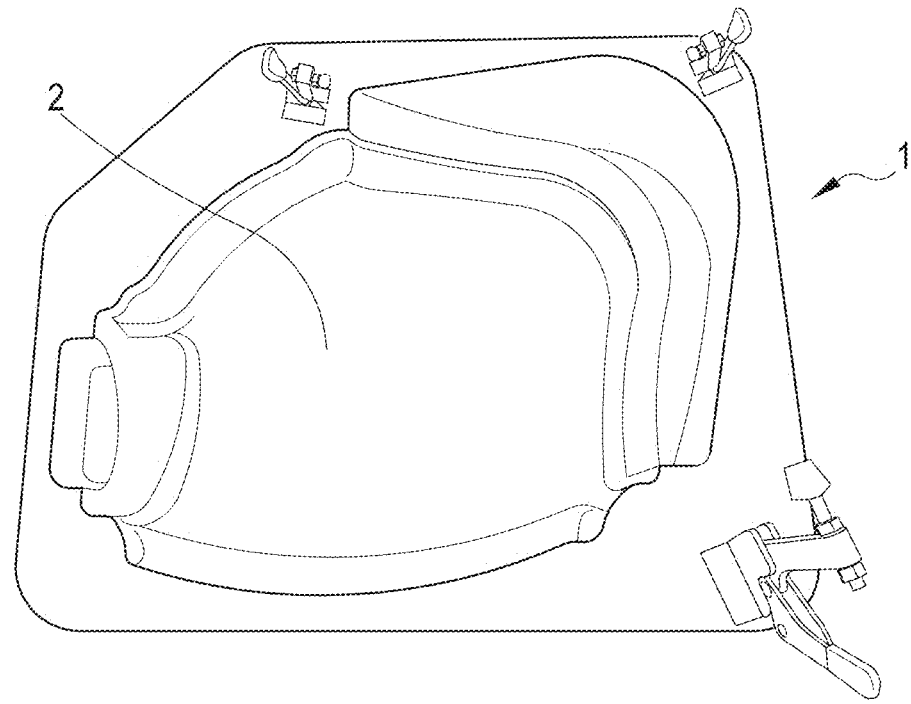
Figure 7:
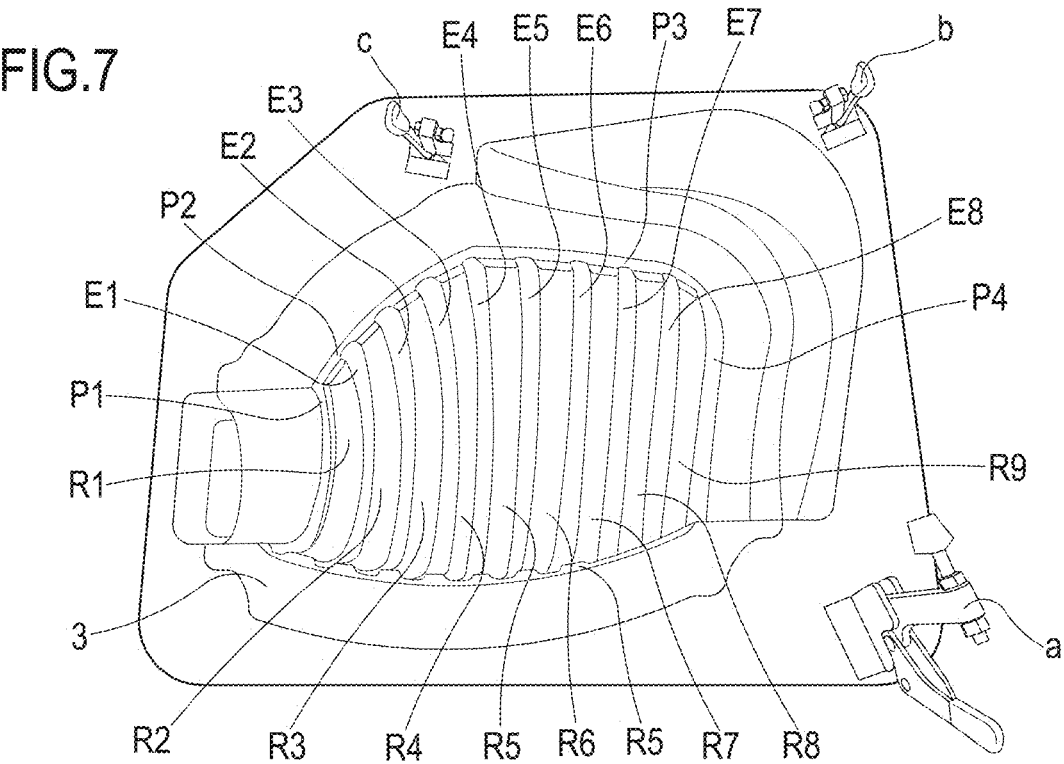

FIG. 6 shows the lower portion of a mould device 1 that serves as a container for containing a concave-shaped base 2, wherein a first portion 3 of a mould (female mould) is housed as shown in FIG. 7.

Figure 8:
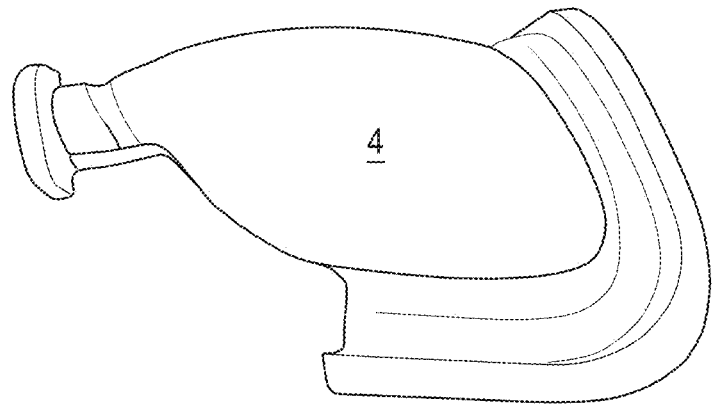
Figure 9:
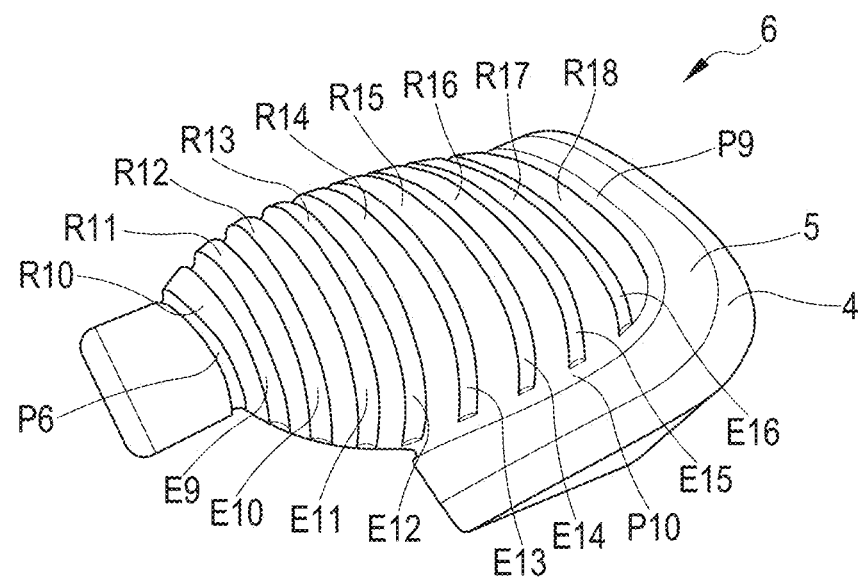

FIG. 8 shows a convex-shaped base 4, on which outer surface a second portion 5 of a mould (male mould) is housed as shown in FIG. 9.

Figure 10:
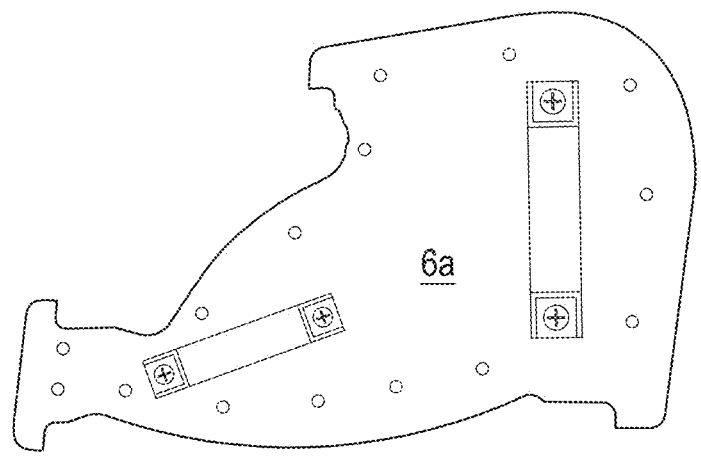

FIG. 10 shows the upper portion 6 of said device 1 acting as a cover.

The lower portion of the device 1 and the upper portion of said device 1 are disposed one above the other in a close arrangement and held together via closing devices signified by the letters a, b and c, shown in FIG. A1.

FIGS. 11 to 25 show a sequence of activities for the preparation of an hemisphere.

Figure 11:
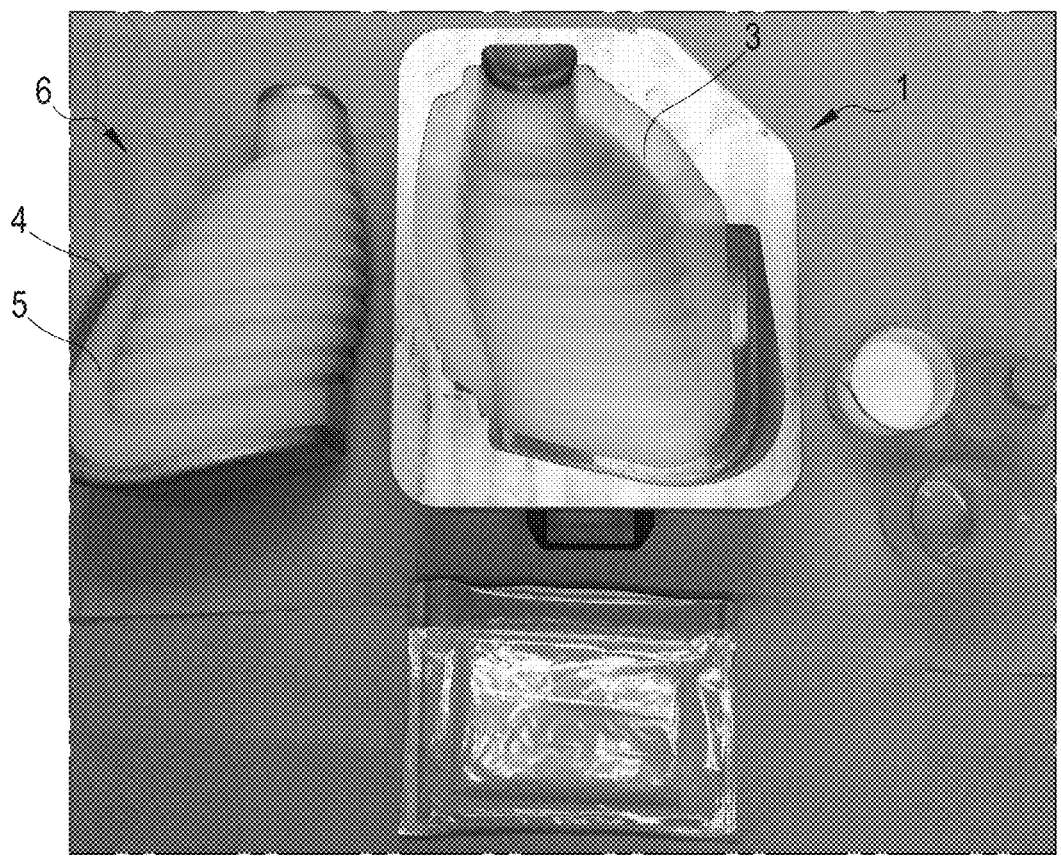
Figure 12:
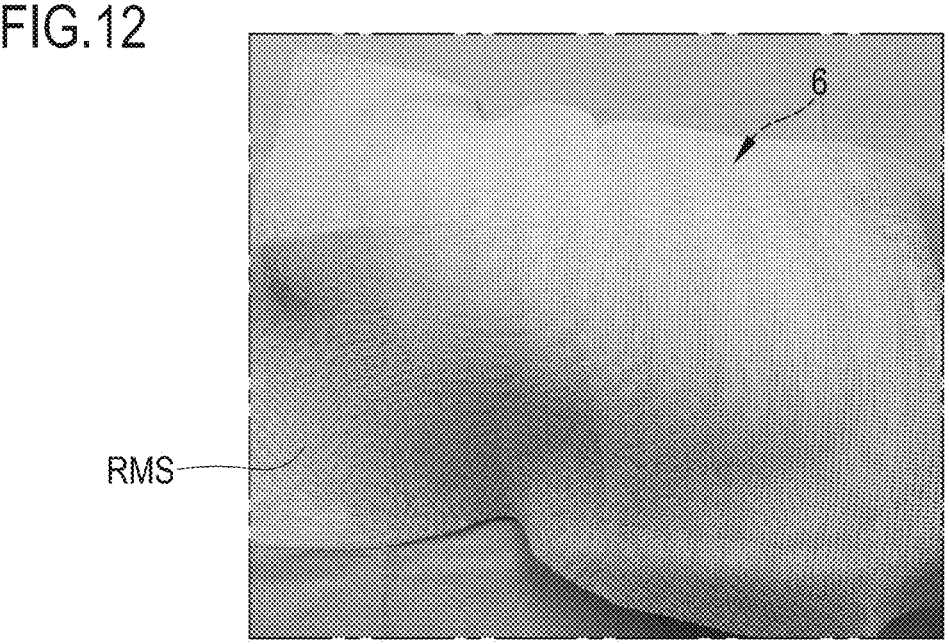
Figure 13:
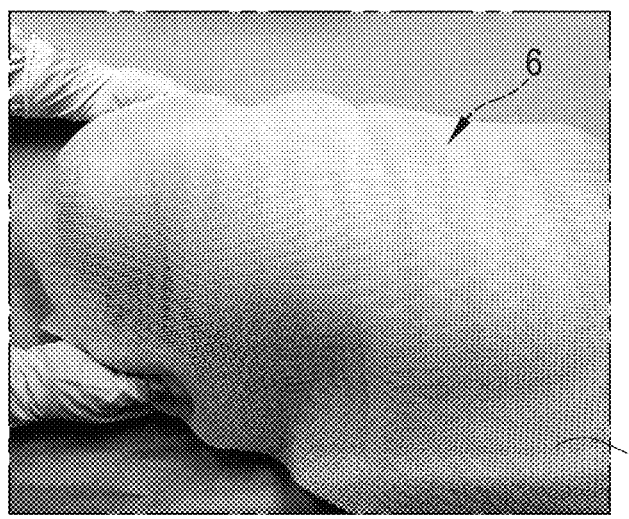
Figure 14:
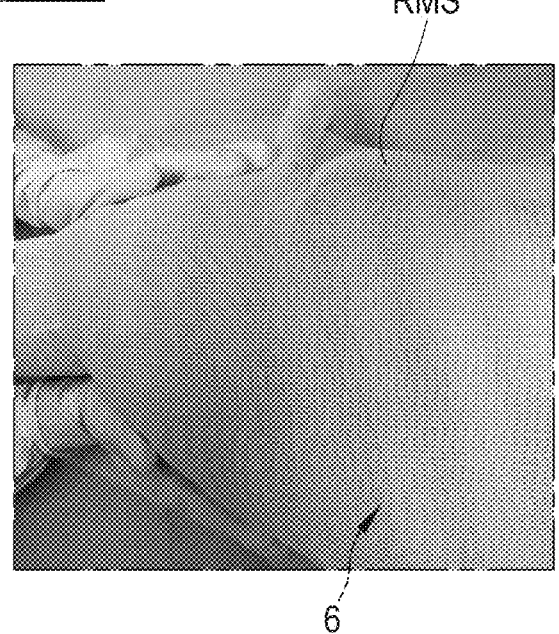
Figure 15:
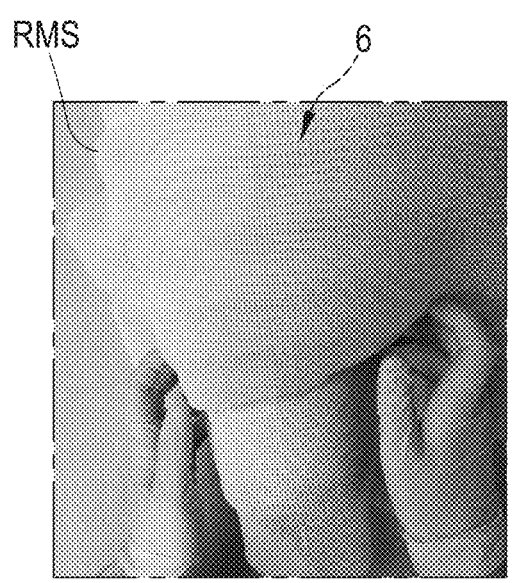
Figure 16:
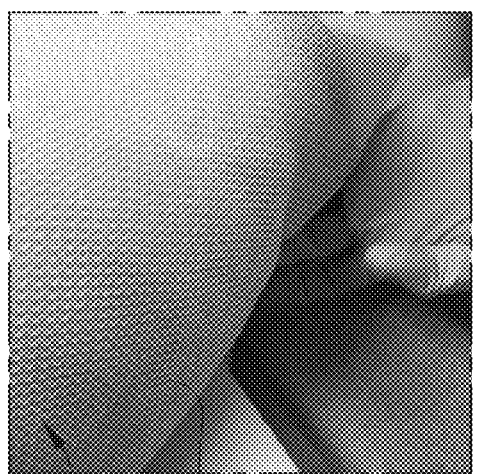
Figure 17:
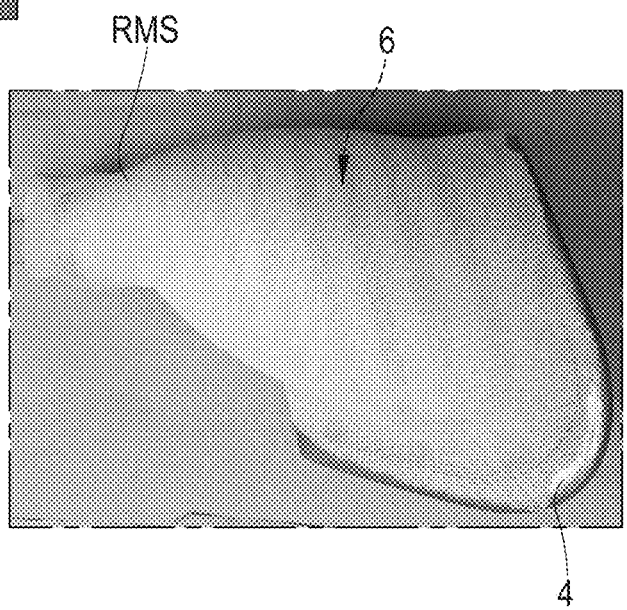

FIG. 11 shows the mould device 1 with a first mould portion 3 (female mould), arranged internally thereof, and a convex-shaped base 4, on which outer surface a second mould portion 5 (male mould) is housed, thereby forming the element 6 of FIG. 9.

FIGS. 12-17 show the element 6 of FIG. 9, whereon the synthetic material meshwork RMS was placed in order to perfectly adhere on the outer surface of a second portion 5 of a mould (male mould).

Figure 18:
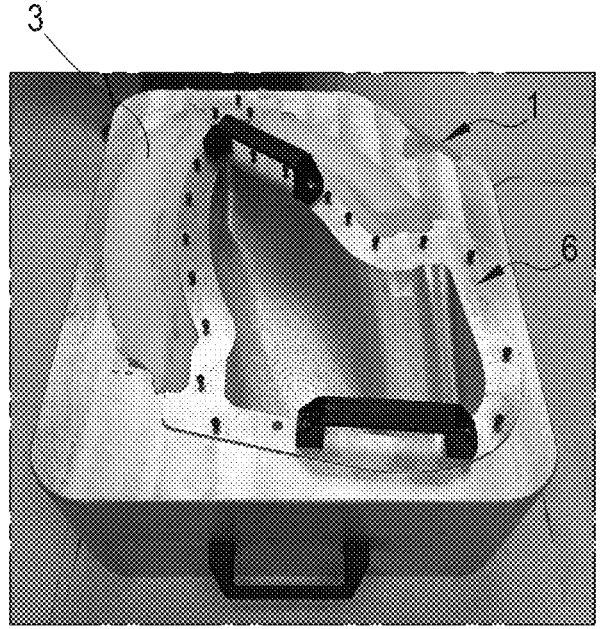

FIG. 18 shows the mould device 1 containing internally thereof a first portion 3 of a mould (female mould) and the cover 6a.

Figure 19:
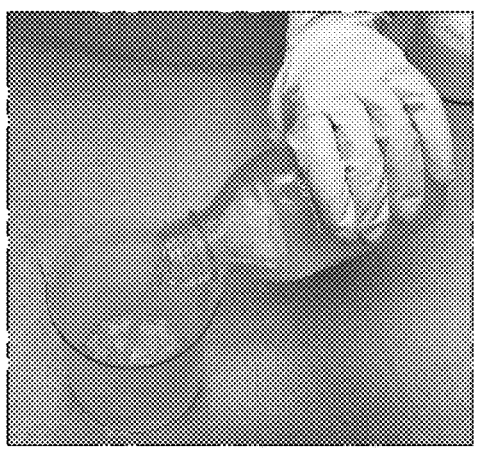
Figure 20:
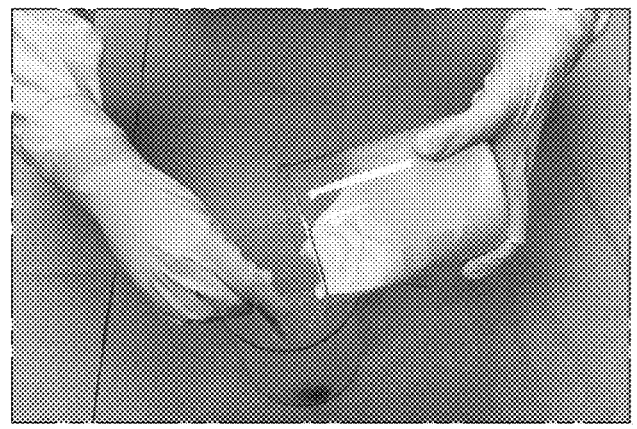

FIGS. 19 and 20 show preparation of the polymeric material.

Figure 21:

FIG. 21 shows pouring of the polymeric material in its liquid state into the mould device 1.

Figure 22:
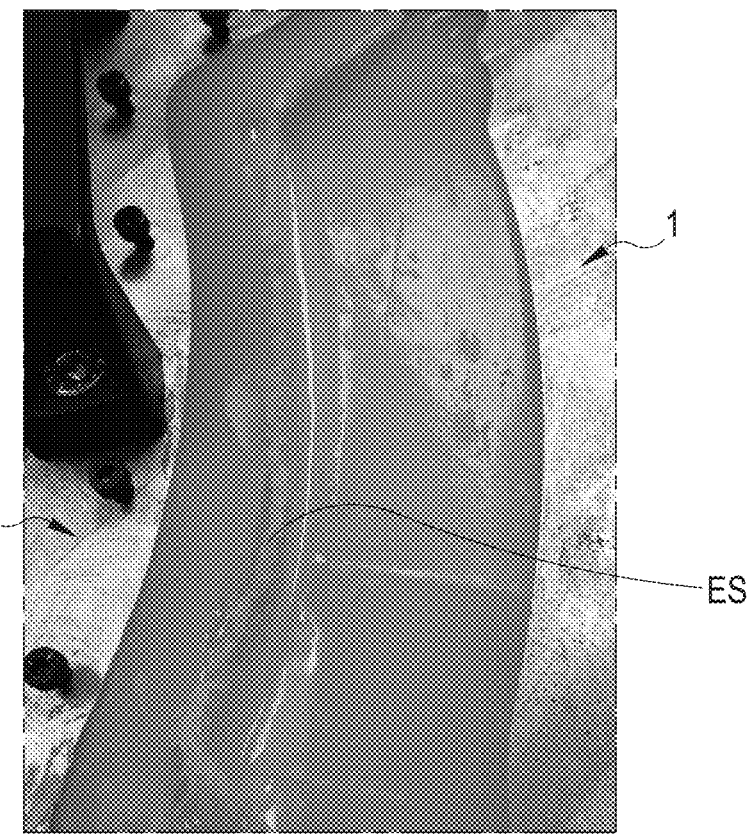

FIG. 22 shows the polymeric material passing from its liquid state to the solid state once the polymeric material was poured and cooled inside the mould device 1.

Figure 23:
Figure 24:
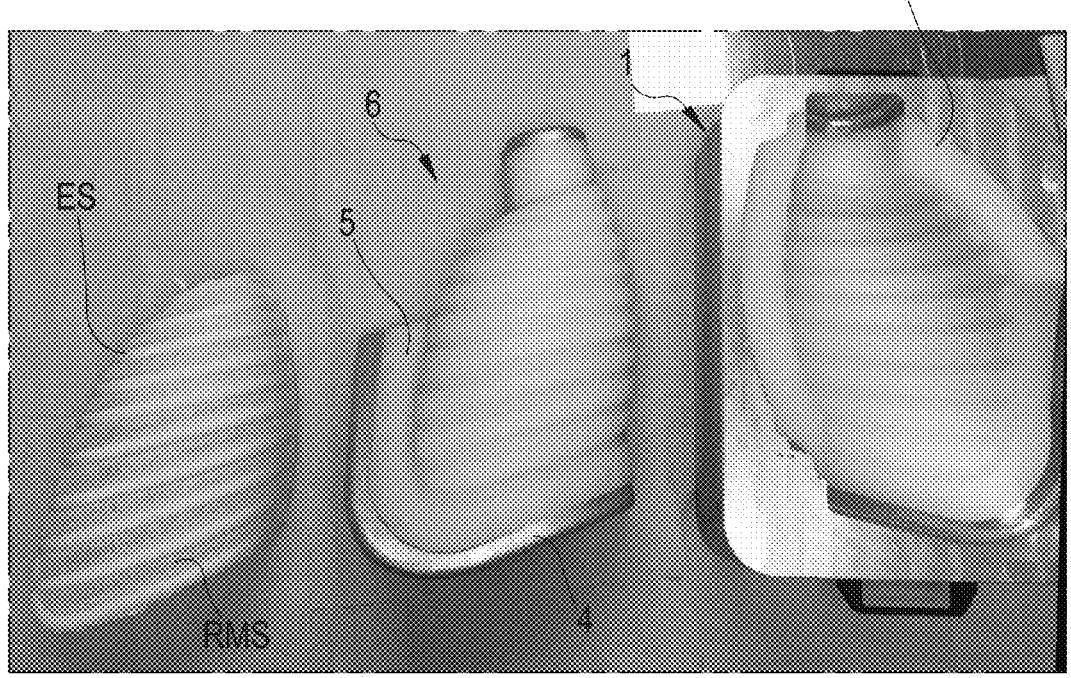

FIGS. 23 and 24 show the right hemisphere extraction ED from the mould device 1 once its preparation is terminated.

Figure 25:
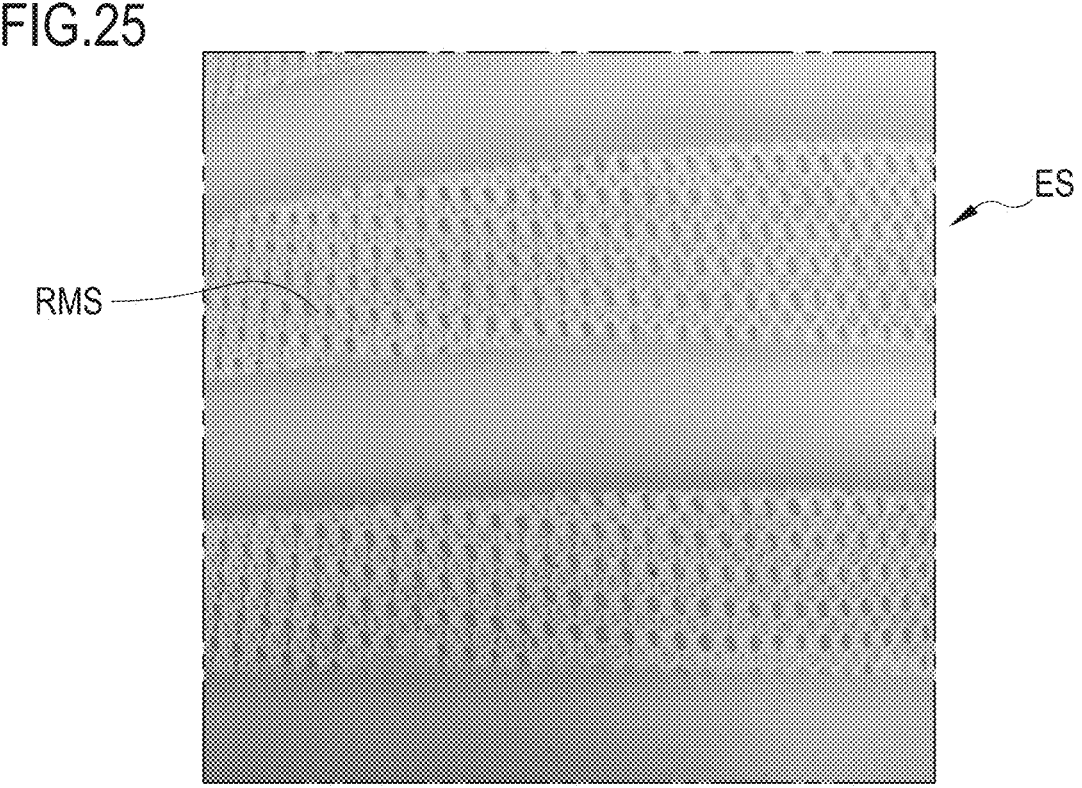

FIG. 25 shows three-dimensionality of the synthetic material meshwork RMS in detail once the same is tensioned between two rib-like elements.

DETAILED DESCRIPTION

The method of preparation of the thoracic prosthesis PT devised by the Applicant allows to prepare said prosthesis in compliance with the specific morphological and structural requirements of each subject. The present invention provides the following:

i) a first mould S, which reproduces the left hemisphere ES comprising a first (female) portion 3 of said mould S and a second (male) portion 5 of said mould S, as well as a method of preparing said mould S;

ii) a second mould S* (not shown in the figure), which reproduces the right hemisphere ED comprising a first (female) portion of said second mould S* and a second (male) portion of said mould S*, as well as a method of preparing said mould S*. It should be appreciated that said mould S*, said first (female) portion and said second (male) portion are all specular to the mould S, to said first (female) portion 3 and to said second (male) portion 5 respectively. Hence, the method of preparation of said mould S* corresponds, in terms of step sequence, to the method of preparation of said mould S and the right hemisphere ED obtained from said mould S*, is prepared with a method corresponding to that used and described for obtaining the left hemisphere ES from said mould S;

iii) a thoracic prosthesis PT which provides joining, in a solidly constrained manner, between said left hemisphere ES, obtained from said first mould S, and said right hemisphere ED obtained from said second mould S*, wherein the segment SG2 of said left hemisphere ES (FIG. 3B) is joined with the segment SG2* of said right hemisphere ED; a method of preparation of said thoracic prosthesis PT is further provided.

The thoracic prosthesis PT referred to in point (iii) is obtained by use of a first mould S, which reproduces the left hemisphere ES and a second mould S*, which reproduces the right hemisphere ED.

The mould S and S* are made solely with materials, that in addition to being biocompatible, allow excellent tightness of the male element with the female element and provide easy detachment once the prosthesis was obtained.

Advantageously, the selected materials are chosen from among the elastomers polysiloxane or soft (i.e. non-rigid) silicone materials. The mould S, reproducing the left hemisphere ES, comprises a first (female) portion 3 of said mould S shown in FIG. 7 and a second (male) portion 5 of said mould S shown a FIG. 9.

Said first (female) portion 3 of said mould S shown in FIG. 7, is a unitary element and exhibits a curved shape about the major axis extending from left to right.

Furthermore, said first (female) portion 3 of said mould S illustrated in FIG. 7, exhibits a plurality of grooves En which is equal to the integer n of ribs taken into account and to be reproduced in the left hemisphere ES, by way of example on the basis of n=8 there is obtained E1-E8. Said grooves En being interspersed from one another and spaced apart by the presence of a plurality of elements in relief Rn+1 arranged in a manner substantially parallel to each other, for example for n=8 there is obtained R1-R9. Each groove En being extended and semicircular in shape, thereby reproducing the shape and the section of a human rib. The elements in relief Rn+1 have a rectangular cross section with rounded corners and are arranged alternately with the grooves En, thereby forming the following structure: R1-E1-R2-E2-R3-E3-R4-E4-R5-E5-R6-E6-R7-E7-R8-E8-R9, see FIG. 7. Between a first element in relief R1 spaced apart from a second element in relief R2, the groove E1 is formed, and so on. It is important that the grooves En present in said first (female) portion 3 of said mould S (FIG. 7), are provided with a concave base with no sharp angles. The same applies to the grooves En present in said second (male) portion 5 of said mould S (FIG. 9). The above is aimed at preventing formation of any irregular shaped ribs or cutting elements.

The grooves E1-E8 are connected to one another via an external groove P1, P2, P3, P4 and P5 (P5 is only hinted at in FIG. 7), which external groove is delimited by the elements in relief R1-R9 and the long sides of the elements in relief R1 and R9.

Said second (male) portion 5 of said first mould S shown in FIG. 9 is a unitary element and exhibits a convex shape about the major axis extending from left to right.

In addition, said second (male) portion 5 of said mould S shown in FIG. 9 exhibits a plurality of grooves E9-E16 arranged in a substantially parallel manner one to another, which are formed by a plurality of elements R10-R18 arranged in substantially parallel manner with each other; the elements R10-R18 have a rectangular cross-section and are arranged in an alternating manner, thereby forming following structure: R10-E9-R11-E10-R12-E11-R13-E12-R14-E13-R15-E14-R16-E15-R17-E16-R18, see FIG. 9. Between a first element R10 spaced from a second element R11, the groove E9 comes to be formed and so on. Said plurality of grooves Sn reproduces the ribs, whilst said plurality of elements in relief Rn+1 reproduces the intercostal space SI existing between at least two of said ribs.

The grooves E9-E16 are connected one to another via an outer groove P6, P7 (not shown in FIG. 9), P8 (not shown in FIG. 9), P9 and P10, which is delimited by the end of the elements in relief R10-R18 and via the long sides of the elements in relief R10 and R18.

Said second (male) portion 5 of said mould S is covered externally by a layer of a synthetic material meshwork RMS (reinforcement meshwork structure RMS) so that the meshwork adheres perfectly and firmly on its outer surface.

The meshwork is preferably a meshwork made of a non-woven polymeric material, composed for example of a polypropylene fiber matrix (SURGIMESH®).

Depending on necessity, a woven polymeric material meshwork may however be also used. The synthetic material meshwork RMS selected for the purposes of the present invention, is preferably a meshwork made of 100% polyester multifilament (P3X and PET2D) or a multifilament combination with 100% polyester monofilament (P4X) known as Surgimesh® (ASPIDE MEDICAL France). The meshwork of selected synthetic material exhibits a perforated and pierced three-dimensional structure that allows tissue integration and drainage of body fluids such as blood and plasma which are formed following implantation of the thoracic prosthesis or a part thereof in a patient. Alternatively it can also be used a polypropylene non-woven fabric 100%, or a warp-knitted polypropylene monofilament mesh 100% or a mixed meshwork, all of them being materials of the known type such as Surgimesh® Esyplug (ASPIDE MEDICAL France).

Subsequently, said second (male) portion 5 of said mould S, shown in FIG. 9, which was coated with said layer of a synthetic material meshwork RMS, is inserted into the cavity formed by said first (female) portion 3 of said mould S shown in FIG. 7, thus being obtained the mould S, which reproduces the left hemisphere ES. Said first portion 3 and said second portion 5 being coupled together and held firmly together.

When said second (male) portion 5 is put in contact with said first (female) portion 3, the elements in relief Rn+1 present on said first (female) portion 3 and said second (male) portion 5, shall be perfectly matching with one another and superimposed, in order that formation of any unwanted passages or irregularities is prevented, which may result in clogging the mesh of the synthetic material meshwork used. A perfect matching and superposition of the grooves Sn is further required, which are present on said first (female) portion 3 and said second (male) portion 5, in order that formation of any ribs with irregular shape or cutting elements may be prevented that may result in a friction with the muscles and organs during breathing once the thoracic PT prosthesis has been implanted.

Finally, the upper portion 6 of said device 1 acting as a cover (FIG. 10), is positioned above the lower portion of said device 1 acting as a container (FIG. 7) of the mould S.

The lower portion of the device 1 (FIG. 7) and the cover 6 of said device 1 (FIG. 10) are disposed one above the other in a close arrangement and held together by means of fastening means and/or clamping devices such as screw terminals a, b and c (see FIG. 7).

At this point the mould S is ready to be used in the method of preparation of a left hemisphere ES.

What disclosed above for the mould S also applies to the mould S*, which reproduces, in a specular manner, the right hemisphere ED.

Figure 1:
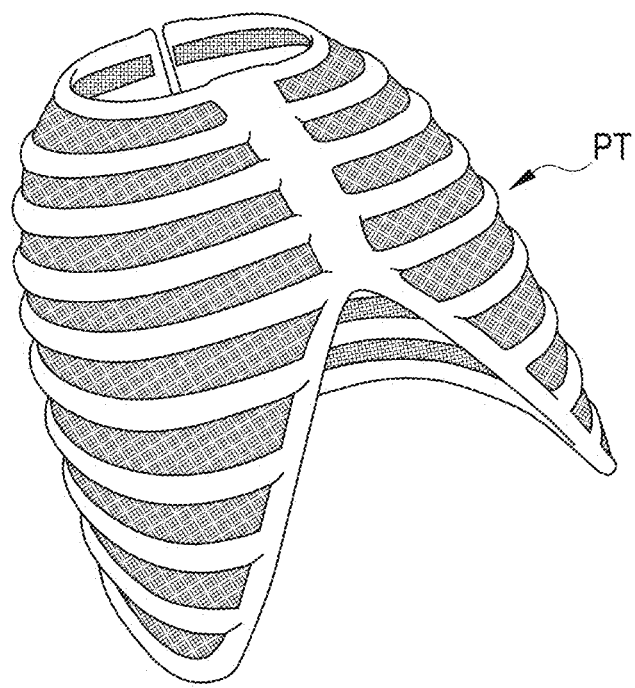
FIG. 1 shows an overall view of a thoracic prosthesis PT, which in this example is a prosthesis of an entire chest. The size of the prosthesis may vary and are decided by the surgeon before the intervention according to the specific needs of each patient.
Figure 2:
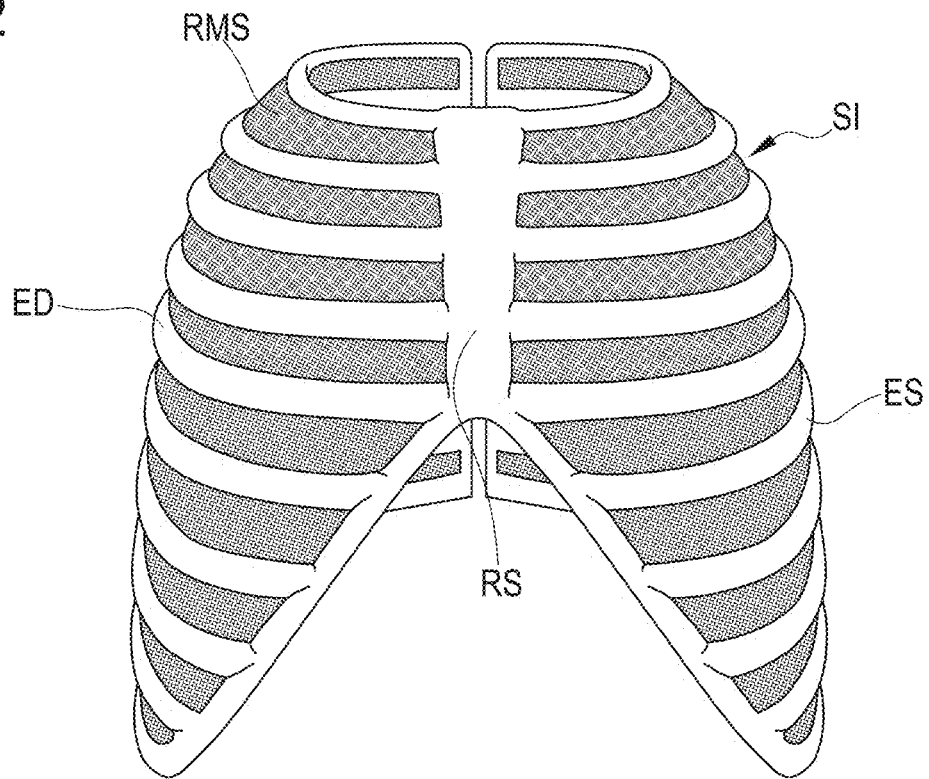
FIG. 2 shows a front view of the thoracic prosthesis PT constituted by a right hemisphere ED and a left hemisphere ES joined together only in the front part by a connection sternal region RS; said right and left hemispheres ED and ES respectively, comprise intercostal spaces SI occupied by a meshwork made of synthetic material RMS (reinforcement mesh-like structure RMS).

Once prepared the right hemisphere ED and the left hemisphere ES according to a method that will be described in a later section, these hemispheres are joined together only at the front thereof through a connection sternal region RS, see FIG. 2.

The left hemisphere ES is prepared with a polymeric composition developed by the Applicant being introduced into the mould S, which mould S has been obtained as previously described; in this manner the volume is filled which was created after that the lower portion of the device 1 (FIG. 7) and the upper portion of said device 1 (FIG. 10) were put in contact with one another in a closed arrangement. On one hand the perfect matching and superposition between the grooves En, for example E1-E8, with the grooves E9-E16, in particular creates a volume through which a layer of synthetic material is disposed, which divides the volume into two portions, see FIG. 3B. This volume is then filled with the polymer composition, thus being tapered elements obtained, which imitate the ribs of the thoracic prosthesis. On the other hand, the perfect matching and superposition between the elements in relief R1-R9 with the elements in relief R10-R19 separated only by the presence of the perfectly adherent layer of synthetic material meshwork RMS, ensures that, after said volume having being filled, the polymeric composition does not infiltrate, thereby impregnating also the portion of said layer of synthetic material meshwork RMS existing between the elements in relief.

The Applicant has devised a polymeric composition, which is the subject of the present invention, comprising:
  a monomer selected from methyl methacrylate (methacrylic acid ester and methanol), and hydroquinone as a stabilizer;
  a polymer selected from the polymethyl methacrylates (PMMA) obtained from the polymers of methyl methacrylate, ester of methacrylic acid.

In common parlance the term methacrylate generally refers to these polymers.

Advantageously, the polymethyl methacrylate has an average molecular weight of about 1,000 Kda.

The polymeric composition is prepared at the time, by disposing the monomer in a first container at room temperature and the polymer in a second container at room temperature.

Subsequently, the contents in liquid form of said first container is put in contact with the contents in solid powder form of said second container, all of that under continuous stirring. The contact of the two contents gives rise to a polymeric exothermic reaction of crosslinking resulting in the formation of a polymeric composition in the liquid state and at low viscosity. Once the two contents have been put in contact with one another, said polymeric composition in its liquid state shall be promptly poured into the mould S, prepared as described above, in order that the volume can be filled, which was created after that the lower portion of the device 1 (FIG. 7) and the upper portion of said device 1 (FIG. 10) were put in contact with one another in a closed arrangement.

It is of the outmost importance that the polymeric composition remains as much as possible in its liquid state and within a certain viscosity range (at an ambient temperature of 25° C.), so as to freely flow through the meshes of the synthetic material meshwork RMS, which is located within the volume created by the perfect matching and superposition between the grooves En, for example, the grooves E1-E8 with the grooves E9-E16.

By flowing in its liquid state through the meshes of the meshwork, the polymeric composition incorporates the latter without creating any inhomogeneities or voids, see FIG. 3B. At the same time the perfect matching and superposition between the elements in relief Rn inside said first (female) portion 3 of said mould S shown in FIG. 7, and inside said second (male) portion 5 of said mould S shown in FIG. 9, prevents the passage of said polymeric composition, while maintaining the free meshwork devoid of any polymer. It is important that the mesh element interposed between said elements in relief Rn remains with its meshes free and without any polymer composition internally thereof, in order to prevent the meshes of the meshwork from becoming occluded, thereby being prevented formation of biological fluids pockets such as blood and plasma or stagnation of the same.

The RMS meshwork, with its three-dimensionality, confers to the synthetic thoracic prosthesis TP notable "scaffolds" characteristics, i.e. of a real scaffold aimed at cells engraftment, mostly mesenchymal cells. In addition, the RMS meshwork inside the synthetic thoracic prosthesis TP is acting as a scaffold also for autologous stem cells from the same patient, since it promotes incorporation thereof. RMS meshwork three-dimensionality allows and helps transposition of the thoracic muscle tissue, furthermore, due to the fact that the meshwork is virtually "poured" and incorporated into the polymeric material used for the synthetic thoracic prosthesis TP thus becoming a single piece, an optimum mechanism during breathing is maintained, which is allowed by RMS meshwork elasticity. The polymeric material used to realize the synthetic thoracic prosthesis TP based on polymethyl methacrylate, has been identified as the best carrier for obtaining aforementioned characteristics, namely to maintain a large free surface for the purpose of cells repopulation, with the "meshwork" being incorporated into a chest hemisphere of high mechanical strength. Finally, the considerable permeability of the prosthesis owing to the meshwork incorporated internally thereof, allows a much more rapid recovery of the patient, thus being prevented any rejection phases and/or formation of fluid (i.e. blood/plasma) pockets which may generate outbrakes and inflammatory processes.

Once all of the polymeric composition was poured, the same is left inside the mould S for a time sufficient to bring the polymer composition from the initial liquid state to a solid state.

At this point the cover 6 of said device 1 (FIG. 10) is removed from the lower portion of said device 1 acting as a container (FIG. 7) of the mould S, thereby obtaining the left hemisphere ES which exhibits a number of ribs Cn (rib-like elements) corresponding to the number n of grooves, said ribs being spaced by said meshwork element portions in a number equal to the elements in relief Rn+1.

The invention claimed is:

1. A synthetic thoracic prosthesis, comprising:
    a plurality of curved rib-like elements spaced apart one from another, each of said rib-like elements having a first end and a second end, the first ends being fixed to a first portion of a perimeter frame, the second ends being fixed to a second portion of the perimeter frame, and
    a continuous reinforcement meshwork structure extending (a) through said rib-like elements and fixed inside the first and second portions of the perimeter frame, and (b) within intercostal spaces formed between said rib-like elements and said perimeter frame; wherein said synthetic thoracic prosthesis includes a concave-shaped inner surface and a convex-shaped outer surface.

2. The synthetic thoracic prosthesis according to claim 1, wherein the continuous reinforcement meshwork structure is tensioned in an extension plane.

3. The synthetic thoracic prosthesis according to claim 1, wherein the continuous reinforcement meshwork structure is perforated or pierced so as to allow tissue integration and the drainage of body fluids.

4. The synthetic thoracic prosthesis according to claim 1, wherein the perimeter frame is formed by a plurality of segments, two of said plurality of segments being spaced apart from one another by the rib-like elements and the intercostal spaces.

5. The synthetic thoracic prosthesis according to claim 1, constituted (a) by a right hemisphere and a left hemisphere joined together, or a portion thereof, or (b) by one of the two hemispheres, or a portion thereof.

6. The synthetic thoracic prosthesis according to claim 5, wherein the right hemisphere and the left hemisphere are joined together via a connection sternal region.

7. The synthetic thoracic prosthesis according to claim 1, wherein the rib-like elements and the perimeter frame are made of a same polymeric material.

8. The synthetic thoracic prosthesis according to claim 1, wherein a perimeter of the synthetic thoracic prosthesis is defined by the perimeter frame.

* * * * *